United States Patent [19]

Horiuchi et al.

[11] Patent Number: 4,818,861
[45] Date of Patent: Apr. 4, 1989

[54] FILM IMAGE READING OUT DEVICE

[75] Inventors: Hideyuki Horiuchi, Abiko; Chiaki Shimbo, Mitaka; Yoichi Onodera, Hachioji; Ryuichi Suzuki, Kokubunji, all of Japan

[73] Assignee: Hitachi Medical Corp., Tokyo, Japan

[21] Appl. No.: 64,573

[22] Filed: Jun. 22, 1987

[30] Foreign Application Priority Data

Jun. 25, 1986 [JP] Japan .................. 61-146944
Jul. 18, 1986 [JP] Japan .................. 61-169517

[51] Int. Cl.⁴ .............................................. H01J 3/14
[52] U.S. Cl. ...................... 250/235; 250/227; 358/208
[58] Field of Search .............. 250/234, 235, 236, 227, 250/578; 358/200, 208; 350/6.6, 6.91

[56] References Cited

U.S. PATENT DOCUMENTS

| 4,010,364 | 3/1977 | Fuwa ........................ 250/234 |
| 4,591,714 | 5/1986 | Goto et al. ................. 250/227 |
| 4,710,624 | 12/1987 | Alvarez et al. ............ 250/235 |

Primary Examiner—Edward P. Westin
Assistant Examiner—Khaled Shami
Attorney, Agent, or Firm—Antonelli, Terry & Wands

[57] ABSTRACT

In a film image reading out device, in which one surface of a film, where images are recorded, is scanned repeatedly with a laser light beam along a scanning line and images are read out by detecting continuously light, which has passed through the film, while moving the film with a low speed in the direction, which is perpendicular to the scanning line, a light diffusing member is disposed closely to the surface opposite to that of the film scanned with the laser light beam and the optical density of the film is detected continuously by leading transmitted and diffused light to a photodetector by means of a bundle of optical fibers.

17 Claims, 3 Drawing Sheets

FILM IMAGE READING OUT DEVICE

BACKGROUND OF THE INVENTION

This invention relates to a film image reading out device, which reads out images on a film by means of laser light, and in particular to a film image reading out device provided with an image signal detecting system, which is suitable for reading out X-ray film images.

There are known various devices for reading out images recorded on an object by scanning linearly the object with a laser light beam and detecting transmitted light, reflected light, etc. coming from the object. Among them the device disclosed in JP-A-55-86970, which is an example, in which fluorescence of the object is measured, excites a fluorescent plate, on which X-ray images are recorded, by scanning it with a laser light beam and detects fluorescence generated thereby in order to read out the recorded images.

On the other hand, in a device reading out images recorded in the form of variations in the density on an X-ray film, etc., the images are read out by scanning the film with a laser light beam and by detecting the amount of the light transmitted by the film. In such a film image reading out device, variations in the optical density of the film constitute image information. However, when the laser light passes through the film, it is diffused. The degree of this diffusion depends on the optical density of the film and if the optical density is 0, the light is almost not diffused. On the contrary, the higher the optical density is, more strongly it is diffused. On the other hand, since there is a limit in the entrance angle of a photodetector, the optical density of the film based on the amount of light measured by the photodetector is different from that obtained by detecting all the diffused light (hereinbelow called diffused light density). That is, the dynamic range of the detected transmitted light is wider than the intrinsic dynamic range of the image on the film.

For this reason, heretofore such a kind of devices requires a photodetector system having a great S/N ratio and a wide dynamic range and moreover an A/D converter having a great number of bits, which digitizes signals. In general there exists no high speed A/D converter having a great number of bits, which was a reason, why it was impossible to obtain a high image reading out processing speed.

SUMMARY OF THE INVENTION

An object of this invention is to provide a film image reading out device permitting the detection of the optical density of images recorded on a film with a wide dynamic range regardless of the limit of the dynamic range of the photodetector system.

Another object of this invention is to provide a film image reading out device having a uniform sensitivity.

One of the features of this invention consists in that in a film image reading out device, in which a film is scanned with a laser light beam in one dimension in order to measure the density of the film, a light slit for preventing re-reflection on a light diffusing plate and the film is disposed between the film and a light collecting system. This light diffusing plate plays a role similar to that of an integrating sphere to diffuse further light, which has passed through the film and has a certain directivity.

The light diffused by this light diffusing plate contains all the light beam information of the light beam diffused by the film before entering the light diffusing plate in all the directions. For this reason, since an amount of light corresponding to the intrinsic optical density of the film can be led to the following light collecting system, it is possible to detect it.

Another feature of this invention consists in that the light collecting system described above comprises a light guiding plate disposed on the light exit side of the film over the whole region scanned with the laser light beam and a bundle of optical fibers leading the light leaving the light guiding plate to the light receiving surface of a photodetector. By using this construction the detection sensitivity is made uniform with respect to the construction, by which the light receiving portion of the bundle of optical fibers is arranged directly in face of the region scanned with the laser light beam and it is possible to reduce stripe-shaped false images in the reproduced image provoked by fluctuations in the sensitivity in the scanning direction with the laser light beam.

DESCRIPTION OF THE PREFERRED EMBODIMENTS

Figure 1:
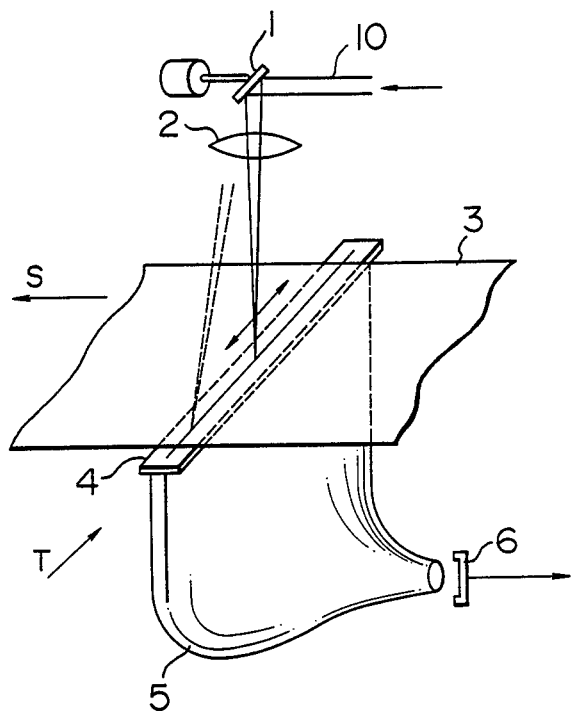
FIG. 1 is a perspective view illustrating the principal part of a film density reading out device, which is an embodiment of this invention.

FIG. 1 is a perspective view illustrating the principal part of a film density reading out device, which is an embodiment of this invention. In the FIGURE, reference numeral 1 represents a light beam sweeping device; 2 a fθ lens; 3 an X-ray film; 4 a transmitting type light diffusing plate; 5 a light collecting system; and 6 a photodetector.

The work of the device according to this embodiment is summarized as follows.

A laser light beam 10 emitted by a laser light source not indicated in the FIGURE is swept with a high speed in one dimension by the light beam sweeping device 1. The scanning of the X-ray film 3 is a one-dimensional constant speed scanning with a laser light beam 10 in the direction T by making it pass through the fθ lens 2. The X-ray film 3 is moved with a low speed in the direction indicated by an arrow S by a film forwarding mechanism not indicated in the FIGURE.

Just behind the X-ray film 3 is located the transmission type light diffusing plate 4 having an appropriate thickness. The laser light beam 10, which has passed through the X-ray film 3, is transformed by this light diffusing plate 4 into a diffused light having no directivity, which is led to the light correcting system 5 following it.

As this light collecting system 5 an optical guide or a bundle of optical fibers arranged in one dimension so constructed that it is long along the one-dimensional scanning direction an be used efficiently. The light exitting end of the light guide or the bundle of optical fibers is formed to be circular or rectangular in order to lead the light beam to the photodetector 6. A photodiode or a photomultiplier tube can be used efficiently as the photodetector 6. Electric signals coming from the photodetector 6 are transformed into digital signals by means of an A/D converter (not shown), and then subjected to necessary signal processings by a signal processor (not shown). On the other hand, the film 3 is forwarded in the direction S perpendicular to the scanning direction with the laser light beam so that it is possible to read out two-dimensional information recorded on the film.

Figure 2:
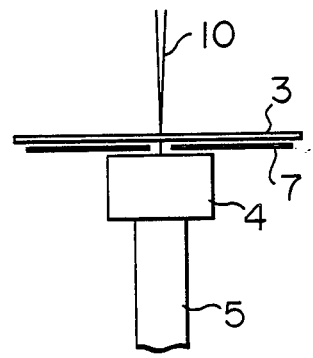
FIG. 2 is a side view seen in the direction indicated by the arrow T in FIG. 1.

FIG. 2 is a side view seen in the direction indicated by the arrow T in FIG. 1. In the FIGURE, reference numerals 3 to 5 indicate constituting elements represented by such reference numerals in FIG. 1. A light slit 7, which is long in the one-dimensional scanning direction, is disposed between the X-ray film 3 and the transmission type light diffusing plate 4, although it is not indicated in FIG. 1. An anti-reflection coating is provided on both the surfaces of the light slit so that the light diffused by the transmission type diffusing plate 4 doesn't return to the X-ray film 3 to be re-reflected by the X-ray film.

An opal plate or a milk white plate made of acryl resin can be used as the transmission type light diffusing plate 4.

Figure 3:
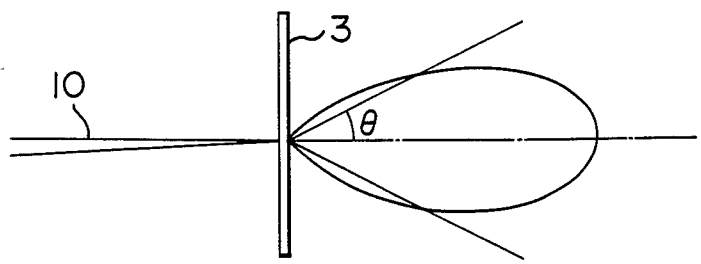
FIG. 3 is a graph indicating the dependence of the light beam diffused by a X-ray film on the angle.

FIG. 3 is a graph indicating the dependence of the intensity of the light, which has passed through a film, on the angle, when a laser light beam impinges on the film. As indicated in the FIGURE, the transmitted light contains a component of diffused light, and the higher the optical density is, the greater the degree of the diffusion is. Consequently the optical density of the film measured by means of a photodetector system having a limited entrance angle indicated by $\theta$ in the FIGURE differs from the diffused light density obtained by measuring the transmitted light over the whole angle of the diffused light.

Here the measured density D can be represented by $$D = \log_{10} \frac{I_o}{I},$$

where $I_o$ and $I$ indicate outputs of the photodetector at the absence and the presence of the film, respectively.

Figure 4:
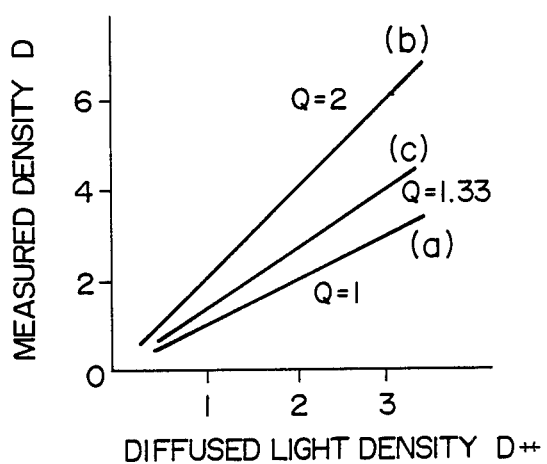
FIG. 4 is a graph indicating the relationship between the diffused light density D ⇂ and the measured density D.

FIG. 4 shows the relationship between the diffused light density D ⫳ and the measured density D. In the FIGURE, (a) corresponds to the case, where all the diffused light is detected (D=D ⫳), and (b) to the case, where only the component, which is approximately parallel to the incident light, is detected (parallel light density).

Therefore the relationship between D and D ⫳ can be represented, in general by using a coefficient Q, by

D=QD⫳.

In a usual film reading out a result indicated e.g. by (c) between (a) and (b) in FIG. 4 is obtained, which differs from (a). For this reason there are problems that a detector system having a dynamic range wider than that of the film image is necessary, that an amplifier having a wide dynamic range and a high S/N ratio is necessary, that an A/D converter, whose number of bits is great, is necessary, etc.

According to the embodiment described above, it is possible to bring the measured density closer to the diffused light density and as a result to make the dynamic range necessary for the photodetector narrower. Concretely speaking, an effect can be obtained that it is possible to read out film images with a high speed, because an A/D converter, which has a small number of bits and a high conversion speed, can be selected.

Further, since the light beam leaving the transmission type diffusing plate 4 is completely diffused, it is sufficiently expanded at the entrance end of the light collecting system 5. Influences of local optical inhomogeneity of the light collecting system, which have been found heretofore, are removed and the light beam leaving the diffusing plate is homogenized. For example, in the case of a light collecting system using optical fibers, if there were no light diffusing plate 4, fluctuations in the light transmission of each of the optical fibers would be observed and a stripe pattern would appear in the read out film image. This drawback is removed by the presence of the diffusing plate. Furthermore, in the case where the regulated position of the light collecting system is more or less deviated, fluctuations in the light output are made smaller by use of the diffusing plate, and the regulation of the optical system including the light beam sweeping system is made easier.

Figure 5:
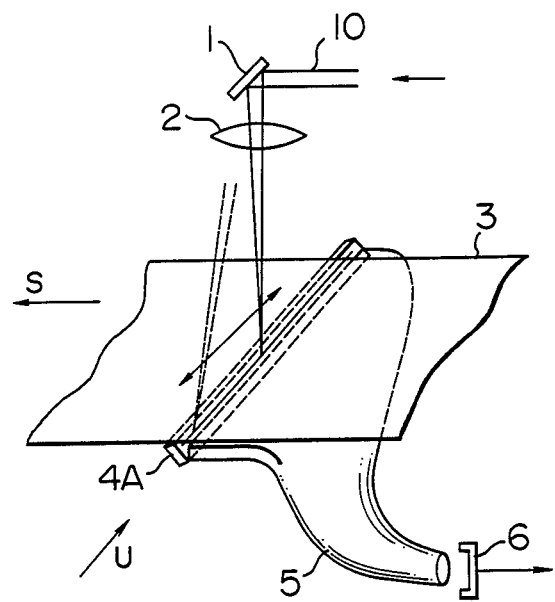
FIG. 5 is a perspective view illustrating the principal part of a film density reading out device, which is another embodiment of this invention.

FIG. 5 is a perspective view illustrating the principal part of a film density reading out device, which is another embodiment of this invention. What differs from the embodiment indicated in FIG. 1 is that a reflection type light diffusing plate 4A is used in this embodiment, while a transmission type light diffusing plate 4 is used in the embodiment indicated in FIG. 1.

The other reference numerals 1–3, 5 and 6 represent the same constituting elements as those indicated in FIG. 1, respectively.

The work of the device according to this embodiment can be summarized as follows.

A one-dimensional constant speed scanning of an X-ray film 3 is effected by an f$\theta$ lens with a laser light beam swept by a light beam sweeping device 1 in one dimension. The X-ray film 3 is moved in the direction indicated by the arrow S.

Just behind the X-ray film 3 is disposed the reflection type light diffusing plate 4A, which reflects the incident light beam to a suitable angle. The laser light beam, which has passed through the X-ray film 3, is transformed into a diffused light having no directivity at all and led to a following light collecting system 5. Since the following working mode is identical to that described for the embodiment indicated in FIG. 1, explanation therefor will be omitted.

Figure 6:
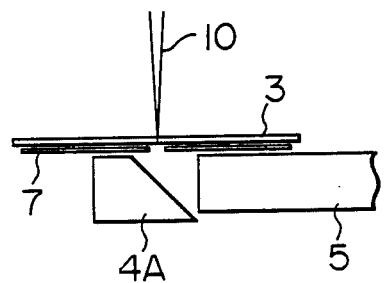
FIG. 6 is a side view seen in the direction indicated by the arrow U in FIG. 5.

FIG. 6 is a side view seen in the direction indicated by the arrow U in FIG. 5. In the FIGURE, the reference numerals 3, 4A and 5 represent the same constituting elements as those indicated in FIG. 5, and 7 indicates a light slit disposed between the X-ray film 3 and the reflection type light diffusing plate 4A, which is long in the one-dimensional light beam sweeping direction. Since the working mode is identical to that of the preceding embodiment, explanation therefor will be omitted.

It is preferable to use, as the reflection type light diffusing plate 4A, a light diffusing plate made of magnesium oxide, etc., which is excellent in the light diffusivity, as used for constructing the inner surface of an integrating sphere.

According to the embodiment described above, similarly to the case of the preceding embodiment, it is possible to bring the measured density closer to the diffused light density, and as the result to make the necessary dynamic range of the photodetector system narrower. In this way an effect can be obtained that an A/D converter, which has a small number of bits and a high conversion speed, can be selected.

Figure 7:
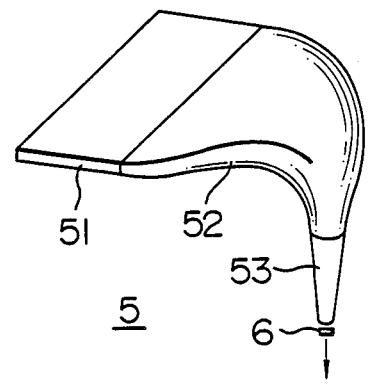
FIG. 7 is a perspective view illustrating more in detail a part of the device indicated in FIG. 1 or 5.

FIG. 7 is a perspective view illustrating a concrete example of the light collecting device in the embodiment indicated in FIG. 1 or 5. That is, light leaving the transmission type light diffusing plate 4 or the reflection type light diffusing plate 4A enters a light conductive plate member 51, repeats total reflections at the inner surface thereof and is led to the exitting end. The light beam leaving the light conductive plate member enters a bundle of optical fibers 52 arranged linearly opposite thereto. The exitting ends of the optical fibers are gathered in a circular form. The light beam leaving the bundle of optical fibers 52 enters a light conductive frustum member 53 disposed in opposition thereto and is transformed into electric signals by a photodetector 6 disposed at the exitting end thereof, after having been focused by a focussing member.

In this construction a plate made of transparent plastic, e.g. acryl resin, can be used as the light conductive plate member 51.

The length of the plate member 51 is adapted to the angle of the light beam focused by the fθ lens 2 and so determined that the light beam, which has passed through the film 3, is sufficiently expanded with respect to the diameter of each of the optical fibers. In this way it is possible to alleviate non-homogeneity of the transmission efficiency due to fluctuations in characteristics or misalignment of the optical fibers. Further, since the diameter of each of the optical fibers can be enlarged, it is possible to reduce the number of the optical fibers and to fabricate the bundle of optical fibers at a low cost The optical fibers can be made of cheap acryl resin, similarly to the plate member, and the bundle of optical fibers 52 are polished and closely contacted with the plate member 51 and the member 53, respectively, so as to conduct the light beam. Since the bundle of optical fibers 52 can be bent freely in the case of necessity, as indicated in the FIGURE, it is possible to make the whole size of the device smaller.

The member 53 can be made also of transparent plastic, e.g. acryl resin. In this way it is possible to use a photodiode, which is smaller than the diameter of the bundle of optical fibers 52. For example, it is possible to obtain a dynamic range wider than that of a photomultiplier by using a small photodiode, which is efficient for reading out of film information having a wide density dynamic range.

In the member 53, since total reflection at the inner surface is utilized, its reflection coefficient and transmission efficiency are great as compared to those of a conical member using a metallic inner surface. Furthermore, since variations in the distribution of the light intensity leaving the bundle of optical fibers can be made smaller, influences of the sensitivity distribution at the surface of the photodetector are reduced.

We claim:

1. A film image reading out device comprising:
   light beam sweeping means for scanning repeatedly a film with a laser light beam along a scanning line of a first direction, the film having opposed surfaces, the laser light beam being projected on one of the opposed surfaces;
   a light diffusing member disposed closely to the surface of said film opposite to that on which said laser light beam is projected, and corresponding to the position of said scanning line, so that light, which has passed through said film, is projected thereon;
   a light transmitting member, which transmits light leaving said light diffusing member, the light diffusing member being positioned so as to have light pass therethrough prior to passing into the light transmitting member;
   a photodetector, which detects light transmitted by said light transmitting member; and
   a film forwarding mechanism, for moving the film in a direction which is perpendicular to said first direction.

2. A film image reading out device according to claim 1, further comprising a plate having a light slit, the plate being positioned such that the light slit is disposed between said film and said light diffusing member, so that only light which has passed through said film enters said light diffusing member.

3. A film image reading out device according to claim 2, in which the plate has a surface, and the surface of the plate has an anti-reflection coating.

4. A film image reading out device according to claim 1, in which said light diffusing member is a transmission type diffusing plate, which diffuses and transmits light entering it.

5. A film image reading out device according to claim 1, in which said light diffusing member is a reflection type diffusing plate, which diffuses and reflects light entering it.

6. A film image reading out device according to claim 1, in which said light transmitting member comprises:
   a light conductive plate member, having opposed sides through which light respectively enters and exits, which receives light leaving said light diffusing member at one side and transmits it to the other side; and
   a plurality of light fibers having two ends, the plurality of light fibers being so disposed that one end of the plurality of light fibers is arranged adjacent to the exit side of said light conductive plate member and coupled optically therewith, and the other end of the plurality of light fibers is bound into a bundle.

7. A film image reading out device according to claim 6, in which said light transmitting member comprises further a frustum member having two ends, one end of which is coupled optically with said other end of said plurality of light fibers bound into a bundle and which frustum member transmits light leaving the other end of the frustum member to said photodetector.

8. A film image reading out device according to claim 1, wherein said light transmitting member has a front end, adjacent the light diffusing member, and a rear end, the light transmitting member being adapted to transmit light from its front end to its rear end, to be applied to the photodetector.

9. A film image reading out device according to claim 8, further comprising a member having a light slit therein, the light slit of the member being positioned such that the light passes through the light slit of the member prior to passing through the light diffusing member.

10. A film image reading out device according to claim 6, wherein said bundle has a circular or rectangular shape.

11. A film image reading out device according to claim 4, wherein the light diffusing member is made of a plate of an acryl resin.

12. A film image reading out device according to claim 11, wherein the plate of an acryl resin is opal or milk white.

13. A film image reading out device according to claim 5, wherein the light diffusing member is a plate made of magnesium oxide.

14. A film image reading out device according to claim 6, wherein the light conductive plate member is a plate made of a transparent acryl resin.

15. A film image reading out device according to claim 7, wherein the plurality of light fibers and the frustum member are each made of acryl resin.

16. A film image reading out device according to claim 2, wherein the plate has two opposed surfaces, one proximate to the film and the other proximate to the light diffusing member, and wherein the two opposed surfaces of the plate have an anti-reflection coating.

17. A film image reading out device according to claim 7, wherein the end of the frustum member optically coupled with the other end of the plurality of light fibers is larger than the other end of the frustum member.

* * * * *